(12) United States Patent
Samaritani et al.

(10) Patent No.: US 8,431,534 B2
(45) Date of Patent: Apr. 30, 2013

(54) GRF-CONTAINING LYOPHILIZED PHARMACEUTICAL COMPOSITIONS

(75) Inventors: Fabrizio Samaritani, Rome (IT); Alessandra Del Rio, Rome (IT)

(73) Assignee: Merck Serono SA, Vaud (CH)

( * ) Notice: Subject to any disclaimer, the term of this patent is extended or adjusted under 35 U.S.C. 154(b) by 335 days.

(21) Appl. No.: 11/744,073

(22) Filed: May 3, 2007

(65) Prior Publication Data

US 2007/0203069 A1   Aug. 30, 2007

Related U.S. Application Data

(63) Continuation of application No. 11/364,079, filed on Mar. 1, 2006, now abandoned, which is a continuation of application No. 10/009,380, filed as application No. PCT/EP00/06061 on Jun. 29, 2000, now abandoned.

(30) Foreign Application Priority Data

Jun. 30, 1999   (EP) .................................... 99112421

(51) Int. Cl.
*A61K 38/25* (2006.01)
*C07K 14/60* (2006.01)

(52) U.S. Cl.
USPC .......................................... 514/11.2; 530/399

(58) Field of Classification Search .................. None
See application file for complete search history.

(56) References Cited

U.S. PATENT DOCUMENTS

| | | | | |
|---|---|---|---|---|
| 4,880,777 A | * | 11/1989 | Momany | ........................ 514/12 |
| 4,963,529 A | | 10/1990 | Fujioka et al. | |
| 5,017,557 A | | 5/1991 | Fabbri et al. | |
| 5,132,401 A | * | 7/1992 | Badamchian | ................ 530/324 |
| 5,352,662 A | * | 10/1994 | Brooks et al. | .................. 514/12 |
| 5,385,738 A | | 1/1995 | Yamahira et al. | |
| 5,863,549 A | | 1/1999 | Tarantino | |
| 6,267,958 B1 | * | 7/2001 | Andya et al. | ............... 424/130.1 |
| 6,284,282 B1 | | 9/2001 | Maa et al. | |
| 2004/0171574 A1 | * | 9/2004 | Morsey et al. | .................. 514/44 |

FOREIGN PATENT DOCUMENTS

| | | |
|---|---|---|
| CA | 2 166 109 | 12/2004 |
| EP | 0 189 673 | 8/1986 |
| EP | 0 300 982 | 1/1989 |
| EP | 0 417 930 | 3/1991 |
| JP | 58023631 | 2/1983 |
| JP | 62-283931 | 12/1987 |
| JP | 3083931 | 4/1991 |
| JP | 04/264020 | 9/1992 |
| JP | 4-330280 | 11/1992 |
| WO | WO-90/11070 | 10/1990 |
| WO | WO-92/18147 | 10/1992 |
| WO | WO-95/35116 | 12/1995 |
| WO | WO-96/19197 | 6/1996 |
| WO | WO-97/04801 A1 | 2/1997 |
| WO | WO-98/53844 | 12/1998 |

OTHER PUBLICATIONS

On-line Medical Dictionary, http://cancerweb.ncl.ac.uk/omd, upon Tyne the CancerWEBProject (published at the Department of Medical Oncology, University of Newcastle, copyright 1997-2004).
Abstract: JP 04 264040 (Yamanouchi Pharm. Co. Ltd., JP) Sep. 18, 1992.
International Search Report mailed Jul. 11, 2000 for Application No. PCT/EP00/06061.
Friedman et al., Int. J. Peptide Protein Res., vol. 37, pp. 14-20 (1991).
Bongers et al., Int. J. Peptide Protein Res., vol. 39, pp. 364-374 (1992).
Bercu, M.D. et al., "Growth Hormone Secretagogues", Serono Symposia USA, Norwell, Massachusetts, U.S.A. (copyright 1996 Springer-Verlag New York, Inc.).

* cited by examiner

*Primary Examiner* — Elizabeth C Kemmerer
*Assistant Examiner* — Regina M Deberry
(74) *Attorney, Agent, or Firm* — Dickstein Shapiro LLP

(57) ABSTRACT

Human growth hormone factor (GFR) containing pharmaceutical compositions are described, and more precisely, lyophilized compositions of hGRF stabilized by means of saccharose.

9 Claims, No Drawings

GRF-CONTAINING LYOPHILIZED PHARMACEUTICAL COMPOSITIONS

CROSS-REFERENCE TO RELATED APPLICATIONS

This is a continuation of U.S. patent application Ser. No. 11/364,079, filed Mar. 1, 2006, which is a continuation of U.S. patent application Ser. No. 10/009,380, filed Apr. 1, 2002, both in the names of Fabrizio Samaritani and Alessandra Del Rio, and entitled GRF-CONTAINING LYOPHILIZED PHARMACEUTICAL COMPOSITIONS.

FIELD OF THE INVENTION

The present invention concerns Growth Hormone Releasing Factor (GRF) containing pharmaceutical compositions. More precisely, it concerns compositions of saccharose-stabilized GRF.

BACKGROUND OF THE INVENTION

In the early 1980's several groups isolated and characterized growth hormone releasing factor (GRF).

GRF (also called Somatorelin) is a peptide secreted by the hypothalamus, which acts on its receptor and can promote the release of growth hormone (GH) from the anterior pituitary. It exists as 44-, 40-, or 37-amino acid peptide; the 44-amino acid form may be converted physiologically into shorter forms. All three forms are reported to be active, the activity residing mainly in the first 29 amino acid residues. A synthetic peptide corresponding to the 1-29 amino acid sequence of human GRF [hGRF(1-29)], also called Sermorelin, has been prepared by recombinant DNA technology as described in European Patent EP 105 759.

Sermorelin has been used in the form of acetate for the diagnosis and treatment of growth hormone deficiency.

GRF has indeed a therapeutic value for the treatment of certain growth hormone related disorders. The use of GRF to stimulate the release of GH is a physiological method in promoting long bone growth or protein anabolism.

It is well known that the natural form of GRF can suffer from chemical degradation in aqueous solution, primarily of Asn at position 8, which results in reduced biological potency (Friedman, A. R. et al., *Int. J. Peptide. Protein Res.*, 37, 14-20, 1991; Bongers, J., et al., *Int. J Peptide. Protein Res.* 39, 364-374, 1992).

The main hydrolytic reactions occurring in GRF are sensitive to pH and reported to be: rearrangement of $Asp^3$, at pH 4-6.5, cleavage of the $Asp^3$-$Ala^4$ bond at pH 2.5-4.5, deamidation and rearrangement of $Asn^8$ at pH above 7 (Felix A. M. et al., *Peptides*, editors: Giralt E. and Andreu D., pp 732-733, Escom Publishers 1991). Due to the combined degradation pathways, unstabilized aqueous solutions GRF are most stable in the pH range 4-5. Bongers et al. (Bongers et al., 1992) have shown that the deamidation reaction at $Asn^8$ increases rapidly as the pH is raised above pH 3.

WO 98/53844 describes stable liquid pharmaceutical compositions of hGRF containing nicotinamide and propylene glycol.

Various workers have made analogues of GRF by substitution of amino acids into the natural GRF sequence to improve the chemical stability (Serono Symposia USA, 1996; Friedman, 1991). While modification can be an effective means to improve the stability and retain bioactivity, it may be undesirable due to altered immunogenicity, which could be a problem for chronic therapies such as growth hormone deficiency.

According to EP 189 673 and U.S. Pat. No. 4,963,529 (Sumitomo Pharma Inc.) GRF formulations can be prepared by lyophilization and stabilized by human serum albumin or glycine. JP 3083931 and EP 417 930 describe a GRF-containing nasal preparation which is rendered low-irritating to nasal mucosa by adding sodium chloride and/or sugar alcohols, such as mannitol or sorbitol thereto.

In order that materials like hGRF be provided to health care personnel and patients, these materials must be prepared as pharmaceutical compositions. Such compositions must maintain activity for appropriate periods of time, must be acceptable in their own right to easy and rapid administration to humans, and must be readily manufacturable. In many cases pharmaceutical formulations are provided in frozen or in lyophilized form. In this case, the composition must be thawed or reconstituted prior to use. The frozen or lyophilized form is often used to maintain biochemical integrity and the bioactivity of the medicinal agent contained in the compositions under a wide variety of storage conditions, as it is recognized by those skilled in the art that lyophilized preparations often maintain activity better than their liquid counterparts. Such lyophilized preparations are reconstituted prior to use by the addition of suitable pharmaceutically acceptable diluent(s), such as sterile water for injection or sterile physiological saline solution, and the like.

Human GRF is found on the market in lyophilized formulations stabilized with mannitol GEREF®, Serono.

DESCRIPTION OF THE INVENTION

We have now found that saccharose confers a better stability to lyophilized formulations of hGRF.

The main object of the present invention is to provide pharmaceutical compositions comprising a solid intimate mixture of human GRF and a stabilizing amount of saccharose.

A further object is to provide a process for the preparation of said pharmaceutical composition, comprising the step of lyophilizing an aqueous solution of the components in the containers. Another object is to provide a presentation form of said pharmaceutical composition comprising the said solid mixture hermetically closed in a sterile condition within containers suitable for storage before use and suitable for reconstitution of the mixture for injectable substances. Such containers may be suitable for single dose administration or for multidose administration. Such lyophilized compositions also preferably contain a bacteriostatic agent. The bacteriostatic agent is preferably m-cresol.

The lyophilized compositions of the invention may further comprise buffering agents. Any buffer which is appropriate for pharmaceutical preparations may be used, for example acetate, phosphate or citrate. The amount of buffering agent to be added to the preparation will be such that the pH of the lyophilized compositions is kept within the desired range after reconstitution. The desired pH range according to this invention is between 2 and 7, preferably between 4 and 6.

Another object is to provide a solution of said solid mixture reconstituted into an injectable solution, such as water for injectable or physiological saline solution. Conveniently such reconstitution is carried out just before use for injection.

There is no critical limitation to the amount of saccharose to be added to the active ingredient, but it will be appropriate to add from 1 to 200 mg/vial, preferably from 20 to 100 mg/vial of saccharose.

According to this invention the word "hGRF" is intended to cover any human GRF peptide, with particular reference to the 1-44, 1-40, 1-29 peptides and the corresponding amides thereof (containing —$NH_2$ at their end) or even a mixture thereof. They are all commercial compounds. The preferred hGRF is hGRF(1-29)-$NH_2$. There is no critical limitation to the amount of active ingredient present in each vial. Such amount is preferably comprised between 0.1 and 100 mg/vial.

The invention will now be described by means of the following Examples, which should not be construed as in any way limiting the present invention.

As shown in these examples, the amount of hGRF can be 3 to 10 mg, the amount of saccharose can be 20.5 to 68.4 mg/vial and the saccharose can be the sole stabilizing agent, and the composition optionally includes excipients.

EXAMPLES

In order to evaluate the excipient's effect on the stability of the active ingredients, three formulations of recombinant hGRF have been prepared with various excipients: saccharose, mannitol and mannnitol/phosphate buffer. The filling volume was 2 ml. The compositions of the various formulations, which were prepared, are reported in Table 1.

TABLE 1

| Formulation | hGRF (mg/ml) | Mannitol (mg/ml) | Saccharose (mg/ml) | Phosphoric Acid (mg/ml) | Sodium Hydroxide |
|---|---|---|---|---|---|
| 1 | 5 | 18.2 | — | — | — |
| 2 | 5 | 18.2 | — | 0.98 | q.s. to pH 4 |
| 3 | 5 | — | 34.2 | — | — |

The preparation of the lyophilizate was performed by dissolving the hGRF bulk powder in the solutions containing the stabilizers. The obtained solutions were filtered and filled into glass vials and lyophilized. The study of the stability of such formulations stored at 40° C. and 50° C. for 4 weeks, was performed by determinations of pH and peptide purity.

The chromatographic assay methodology (reverse phase HPLC) to evaluate the purity of hGRF was a gradient elution through a C-18 column, using a mobile phase (TFA/water/acetonitrile) at 1 ml/min and UV detection at 214 nm.

The pH was determined by a pH meter on vials reconstituted with 5 ml of water for injection.

The results are summarized in Tables 2 and 3.

TABLE 2

| | | pH | | | | |
|---|---|---|---|---|---|---|
| | | 40° C. | | 50° C. | | |
| Formulation | T = 0 | 3 weeks | 4 weeks | 2 weeks | 3 weeks | 4 weeks |
| 1 | 6.8 | 7.4 | 7.4 | 7.2 | 7.3 | 7.4 |
| 2 | 4.8 | 5.2 | 5.4 | 5.6 | 5.4 | 5.7 |
| 3 | 5.5 | 5.4 | 5.5 | 5.4 | 5.4 | 5.4 |

TABLE 3

| | | Peptide Purity (%) | | | | |
|---|---|---|---|---|---|---|
| | | 40° C. | | 50° C. | | |
| Formulation | T = 0 | 3 weeks | 4 weeks | 2 weeks | 3 weeks | 4 weeks |
| 1 | 97.7 | 96.3 | 95.7 | 93.7 | 92.9 | 91.8 |
| 2 | 97.7 | 95.6 | 94.8 | 89.4 | 88.5 | 84.2 |
| 3 | 97.8 | 97.9 | 97.8 | 97.8 | 97.8 | 97.6 |

Results showed that the formulation containing saccharose presented a better stability profile when compared to the formulations containing mannitol or mannitol/phosphate buffer.

Additional formulations having the composition of formulation 3 described in Table 1 were manufactured in different containers (vials); the composition is reported in Table 4.

TABLE 4

| Formulation | hGRF (mg/vial) | Saccharose (mg/vial) |
|---|---|---|
| 3a | 3 | 20.5 |
| 3b | 10 | 68.4 |

The formulations were stored at 5° C., 25° C. and 40° C. and tested for stability using the analytical methods described before (pH, purity and titre by RP).

Stability data have been generated up to 24 weeks; the results are reported in Tables 5 to 7.

TABLE 5

| | | pH | | |
|---|---|---|---|---|
| Formulation | T = 0 | 5° C. 4 weeks | 25° C. 4 weeks | 40° C. 4 weeks |
| 3a | 4.95 | 5.03 | 5.02 | 5.12 |
| 3b | 4.96 | 5.09 | 5.06 | 5.13 |

TABLE 6

| | Formulation 3a Storage Temperature = 40° C. | | | | |
|---|---|---|---|---|---|
| Test | 0 Time | 4 weeks | 8 weeks | 12 weeks | 24 weeks |
| Purity (%) | 97.8 | 97.8 | 97.3 | 97.0 | 96.0 |
| Assay (mg/vial) | 2.8 | 2.9 | 2.9 | 2.8 | 2.9 |
| pH | 4.95 | 5.12 | 5.25 | 5.30 | 5.43 |

TABLE 7

Formulation 3b
Storage Temperature = 40° C.

| Test | 0 Time | 4 weeks | 8 weeks | 12 weeks | 24 weeks |
|---|---|---|---|---|---|
| Purity (%) | 97.9 | 97.9 | 97.4 | 97.1 | 95.1 |
| Assay (mg/vial) | 9.8 | 9.8 | 10.0 | 9.8 | 8.8 |
| pH | 4.96 | 5.13 | 5.16 | 5.38 | 5.53 |

The stability of reconstituted solutions with 1.5 and 5 ml 0.3% m-cresol at 5±3° C. and 25±2° C. up to 1 month was also studied.

The stability data on the reconstituted solutions are reported in Tables 8 to 10.

TABLE 8

| Formulation | Storage (° C.) | pH T = 0 | 1 week | 2 weeks | 3 weeks | 4 weeks |
|---|---|---|---|---|---|---|
| 3a | 5° C. | 4.94 | 5.03 | 5.04 | 5.05 | 5.18 |
| 3b | 5° C. | 4.96 | 5.07 | 5.04 | 5.14 | 5.25 |
| 3a | 25° C. | 4.94 | 5.05 | 5.07 | 5.07 | 5.19 |
| 3b | 25° C. | 4.96 | 5.14 | 5.12 | 5.14 | 5.24 |

TABLE 9

| Formulation | Storage (° C.) | Peptide Purity (%) T = 0 | 1 week | 2 weeks | 3 weeks | 4 weeks |
|---|---|---|---|---|---|---|
| 3a | 5° C. | 97.6 | 97.6 | 97.5 | 97.6 | 97.4 |
| 3b | 5° C. | 97.6 | 97.5 | 97.4 | 97.5 | 97.4 |
| 3a | 25° C. | 97.6 | 96.4 | 95.4 | 94.5 | 93.5 |
| 3b | 25° C. | 97.6 | 96.3 | 95.4 | 94.7 | 93.5 |

TABLE 10

| Formulation | Storage (° C.) | Peptide Content (mg/vial) T = 0 | 1 week | 2 weeks | 3 weeks | 4 weeks |
|---|---|---|---|---|---|---|
| 3a | 5° C. | 2.9 | 3.0 | 2.5 | 3.0 | 2.9 |
| 3b | 5° C. | 9.6 | 10.0 | 9.1 | 10.0 | 9.9 |
| 3a | 25° C. | 2.9 | 2.9 | 2.8 | 2.8 | 2.8 |
| 3b | 25° C. | 9.6 | 10.0 | 9.3 | 9.5 | 9.4 |

EXAMPLE OF PHARMACEUTICAL MANUFACTURING

Materials: extra pure saccharose DAB, Ph Eur, BP, NF (Merck); water for injectables.

As containers have been used vials DIN 2R and DIN 6R (borosilicate glass type I), rubber closures (Pharmagummi W1816 V50) and aluminum rings and flip-off caps (Pharma-Metal GmbH).

Preparation of hGRF Solution Containing Saccharose:
(for 200 vials containing each 3 or 10 mg hGRF).

Saccharose (17.1 g) are dissolved into water for injectables (500 ml) in order to obtain the starting saccharose solution.

The bulk of the hGRF 2 g) is added to the saccharose solution so as to obtain a final weight of 400 g the solution is filtered through a 0.22 μm Durapore sterile filter (Millipore).

Filling Up and Lyophilization

The vials are filled up with 0.6 and 2 ml of hGRF sterile solution, transferred to the freeze-dryer and lyophilized according to the following cycle:

freezing:
 −25° C. for 3 hrs
 −15° C. for 1 hr
 −45° C. for 3 hrs
primary drying: −10° C. for 13 hrs
secondary drying: from −10° C. to +40° C. in 8 hrs; +40° C. till end of cycle

The invention claimed is:

1. A product which is a vial containing a pharmaceutical composition consisting of a lyophilized mixture of 3 to 10 mg/vial of human growth releasing factor (hGRF), 20.5 to 68.4 mg/vial of saccharose, and a buffering agent in an amount sufficient such that the pH is 4 to 6 when said lyophilized mixture is reconstituted in a solvent or solution.

2. The product according to claim 1 wherein the pharmaceutical composition contains 3 mg/vial of hGRF and 20.5 mg/vial of saccharose.

3. The product according to claim 2 in which the hGRF is recombinant hGRF.

4. The product according to claim 2, wherein the vial is hermetically closed in a sterile condition, and is suited for a storage before use and for reconstitution of the mixture into a solvent or into a solution for injectables.

5. The product according to claim 1, wherein the pharmaceutical composition contains 10 mg/vial of hGRF and 68.4 mg/vial of saccharose.

6. The product according to claim 5 in which the hGRF is recombinant hGRF.

7. The product according to claim 5, wherein the vial is hermetically closed in a sterile condition, and is suited for a storage before use and for reconstitution of the mixture into a solvent or into a solution for injectables.

8. The product according to claim 1, wherein the vial is hermetically closed in a sterile condition, and is suited for a storage before use and for reconstitution of the mixture into a solvent or into a solution for injectables.

9. The product according to claim 1 in which the hGRF is recombinant hGRF.

* * * * *